(12) United States Patent
Guo et al.

(10) Patent No.: US 6,537,781 B1
(45) Date of Patent: Mar. 25, 2003

(54) METHODS AND COMPOSITIONS CONCERNING CANINE INTERLEUKIN 5

(75) Inventors: Hongliang Guo, Scarborough; Robert Lawton, Gorham; Brion Mermer, Cumberland; Ashok P. Aiyappa, Falmouth, all of ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/371,615

(22) Filed: Aug. 10, 1999

(51) Int. Cl.[7] .................. C12N 15/00; C12N 15/09; C12N 5/00
(52) U.S. Cl. ............... 435/69.52; 435/69.1; 435/320.1; 435/325; 435/252.3; 435/254.11; 435/69.5; 536/23.1; 536/23.5
(58) Field of Search .......................... 536/24.31, 23.1, 536/23.5; 435/320.1, 69.1, 69.5, 69.52, 325, 252.3, 254.11

(56) References Cited

U.S. PATENT DOCUMENTS 5,593,861 A 1/1997 Maeda et al. ............... 435/69.1

FOREIGN PATENT DOCUMENTS

| WO | WO-9700321 | * 1/1997 | ................ 435/69.5 |
| WO | 97/30156 | 8/1997 | |
| WO | 9961618 | 2/1999 | |

OTHER PUBLICATIONS

Alberts et al. Molecular Biology of the Cell. 2nd Edition Garland Publishing, Inc. New York and London (1989).*
Darnell et al. Molecular Cell Biology. Scientific American Books. Freeman and Company New York (1986).*
Wells, JA Additivity of Mutational Effects in Proteins. Biochemistry 29:8509–8517 (1990).*
Yan et al. Two–Amino Acid Molecular Switch in an Epithelial Morphogen That Regulates to Two District Receptors. Science 290:523–527 (2000).*
Bowie et al. Deciphering the Message in Protein Sequences: Tolerance to Amino Acid Substitutions. Science 247:1306–1310 (1990).*
Padrid, Philip A., et al.; Sequence and Structural Analysis of Feline Interleukin–5 cDNA; American Journal Veterinary Research, vol. 59: No. 10, Oct. 1998 (7 pages).
Mertens, Bea, et al.; Tbe Nucleotide Sequence of the Bovine Interleulin–5–encoding cDNA; Gene: An International Journal on Genes and Genomes, vol. 176, No. 1–2. Oct. 17, 1996, pp. 273–274.
Chihiro, Azuma et al.; Cloning of cDNA for human T–cell replacing factor (interleukin–5) and Comparsion with the Murine Homologue, Nucleic Acids Research, vol. 14, No. 22, 1986, pp. 9149–9158.
Cuss et al., "Inhibition of interleukin–5 with a monoclonal antibody attenuates allergic inflammation," *Allergy* 52:787–794 (1997).
Desreumaux et al., "Eosinophils in allergic reactions," *Current Opinion in Immunology* 8:790–795 (1996).
Fabian et al., "Activation of human eosinophil and neutrophil functions by haematopoietic growth factors: Comparsions of IL–1, IL–3, IL–5 and GM–CSF,"–0 *British Journal of Haematology* 80:137–143 (1992).
Kopf et al., "IL–5–deficient mice have a development defect in CD5+ B–1 cells and lack eosinophilia but have normal antibody and cytotoxic T cell responses," *Immunity* 4:15–24 (1996).
Persson et al., "'Ultimate activation' of eosinophils in vivo: Lysis and release of clusters of free eosinophil granules (Cfegs)," *Occasional Review* pp. 571–574.
Persson et al., "Eosinophil lysis and free granules: an in vivo paradigm for cell activation and drug development," *Trends in Pharmalogical Science* 18:117–123 (1997).
Rothenberg, "Eosinophilia," *New Engl. Journal of Medicine* 338(22):1592–1600 (1998).
Weller et al., "Role of the eosinophil in allergic reactions," *Eur. Respir.* J. 9:109s–115s (1996).
Yang et al., "Depletion of eosinophil infiltration by anti–IL–5 monoclonal antibody (TRFK–5) accelerates open skin wound epithelial closure," *Am. Journ. of Pathology* 151(3):813–819 (1997).
Riechmann, Lutz, et al.; Reshaping Human Antibodies for Therapy; Nature, vol. 332; Mar. 24, 1988 (5 pages).
Takatsu, K. et al.; Interleukin 5 and its Receptor; Progress in Growth Factor Research, vol. 3; pp. 87–102; 1991; pp. 87–102.
GenBank Accession No. AF091133 Aug. 4, 1999.
International Preliminary Examination Report for corresponding application PCT/US00/21651.
International Search Report for corresponding application PCT/US00/21651.

* cited by examiner

*Primary Examiner*—Elizabeth Kemmerer
*Assistant Examiner*—Regina M. DeBerry
(74) *Attorney, Agent, or Firm*—McDonnell Boehnen Hulbert & Berghoff

(57) ABSTRACT

The present invention provides the nucleotide and amino acid sequences of canine IL-5. It also sets forth a recombinant DNA molecule, and conservative variants thereof, comprising the DNA sequence of canine IL-5, and recombinant vectors such as expression vectors, comprising a DNA sequence encoding canine IL-5. Further, the invention sets forth polypeptides produced using a recombinant expressio vector containing a canine IL-5 sequence. Also disclosed are compositions comprising a nucleotide sequence that is antisense to a DNA sequence encoding a component of canine IL-5, wherein the component can be the full canine IL-5 protein. Disclosed are a cloning vector comprising a DNA sequence of canine IL-5 cDNA material; a recombinant cell line comprising a DNA sequence of the canine IL-5 cDNA material; a method for producing a polypeptide comprising a step of expressing a peptide comprising an amino acid sequence encoded by a cloning vector comprising canine IL-5 cDNA material; and a cell that expresses a recombinant polypeptide encoded by a DNA sequence (or conservative variants thereof) that encodes canine IL-5 or components thereof. Furthermore, antibodies that bind to canine IL-5, and mimetopes of IL-5 epitopes are also disclosed.

11 Claims, 2 Drawing Sheets

Figure 1

CANINE IL-5 COMPLETE CODING SEQUENCE

Nucleic Acid Sequence: (SEQ ID NO:1)

```
5'1    atgagaatgc ttctgaattt gagtttgcta gctcctgggg ctgcctatgt ttctgccttt    60
 61    gctgtagaaa atcccatgaa tagactggtg gcagagacct tgacactgct ctccactcat   120
121    cgaacttggc tgataggcga tgggaacctg atgattccta atagacacat taaaaatcac   180
181    caactgtgca ttaaagaagt tttcagggt atagaaacca tgaagaacca aactgcccac   240
241    ggggaggctg tggataaact attccaaaac ttgtctttaa taaaagaaca catagagcgc   300
301    caaaaaaaa ggtgtgcagg agaaagatgg agagtgacaa agttcctaga ctacctgcaa   360
361    gtattccttg gtgtaataaa caccgagtgg acaatggaaa gttga                   405
```

Amino Acid Sequence: (SEQ ID NO:2)

```
  1  Met Arg Met Leu Leu Asn Leu Ser Leu Leu Ala Leu Gly Ala Ala Tyr   16
 17  Val Ser Ala Phe Ala Val Glu Asn Pro Met Asn Arg Leu Val Ala Glu   32
 33  Thr Leu Thr Leu Leu Ser Thr His Arg Thr Trp Leu Ile Gly Asp Gly   48
 49  Asn Leu Met Ile Pro Thr Arg His Ile Lys Asn His Gln Leu Cys Ile   64
 65  Lys Glu Val Phe Gln Gly Ile Glu Thr Met Lys Asn Gln Thr Ala His   80
 81  Gly Glu Ala Val Asp Lys Leu Phe Gln Asn Leu Ser Leu Ile Lys Glu   96
 97  His Ile Glu Arg Gln Lys Lys Arg Cys Ala Gly Glu Arg Trp Arg Val  112
113  Thr Lys Phe Leu Asp Tyr Leu Gln Val Phe Leu Gly Val Ile Asn Thr  128
129  Glu Trp Thr Met Glu Ser                                           134
```

Figure 2

IL-5 AMINO ACID SEQUENCE COMPARISONS BETWEEN HUMAN (SEQUENCE 1; SEQ ID NO:7), MOUSE (SEQUENCE 2; SEQ ID NO:8) AND DOG (SEQUENCE 3; SEQ ID NO:2)

1  MR-MLLHLSLLALGAAYVYAIPT--EIPTSALVKETLALLSTHRTLLIA--NETLRIPVPVHKNHQLCTEEI...

2  MRRMLLHLSVLTLSC--VWA--TANEIPMSTVVKETLTQLSAHRALLTS--NETMRLPVPTHKNHQLCIGEI...

3  MR-MLLNLSLLALGAAYVSAFAV--ENPMNRLVAETLTLLSTHRTWLIGDGN--LMIPTPENKNHQLCIKEV...

1  FQG--IGTLESQTVQGTVERLFKNLSLIKKYIDGQKKKC--GEEERRRVNQFLDYLQEFLGVMNTEWIIES*

2  FQGLDI--LKNQTVRGGTVEMLFQNLSLIKKYIDRQKEKCGEEERRRTRQFLDYLQEFLGVMSTEWAMEG*

3  FQG--IDTLKNQTAHGEAVDKLFQMLSLIKEHIERQKKRCAGE-RWRVTKFLDYLQVFLGVINTEWIMES*

Pairwise comparisons:
human (1) mouse (2)   69%
human (1) dog   (3)   65%
mouse (2) dog   (3)   59%

METHODS AND COMPOSITIONS CONCERNING CANINE INTERLEUKIN 5

FIELD OF THE INVENTION

This application reports the isolation and characterization of canine interleukin-5 ("IL-5") and includes nucleic and amino acid sequences therefor. More particularly, it concerns a nucleic acid sequence which comprises DNA which encodes canine interleukin-5.

BACKGROUND

Interleukin 5

Interleukin-5 (IL-5) has been studied in both human and murine systems. It was initially designated T cell-replacing factor or B cell growth factor II (BCGF II). IL-5 is understood to induce or mediate multiple effects. It promotes the proliferation of activated B lymphocytes as well as the generation of both IgM and IgG responses. IL-5 also promotes IgA secretion, apparently by acting on cells that already express surface IgA.

IL-5 cDNA clones from mouse and human species have been isolated. See Takatsu, K., and Tominaga, A., "Interleukin 5 and its Receptor", *Progress in Growth Factor Research*, 3: 87–102 (1991), incorporated herein by reference. Mouse IL-5 consists of 133 amino acid residues, including a signal sequence of 21 residues and three sites for N-glycosylation. In contrast, human IL-5 consists of 139 amino acid residues, including a signal sequence of 22 residues and two sites for N-glycosylation. Both mouse and human IL-5 exist as a dimer linked by disulfide bond. Further, mouse and human IL-5 are 71% homologous at the amino acid level. However, while human IL-5 is capable of stimulating mouse cells, mouse IL-5 is only weakly cross-reactive with human cells.

Prior to this invention, no canine IL-5 DNA or amino acid sequence has been reported. It is unknown whether canine IL-5 will cross react with human or mouse cells.

In Vitro Activities

In humans IL-5 is known to exert most of its biological activities on hematopoietic lineages outside the lymphoid compartment. This cytokine acts as an eosinophil stimulating factor; e.g., it augments the number of eosinophil colonies that develop in semisolid bone marrow cultures. IL-5 is a potent regulator of eosinophilia and appears to act on relatively mature progenitors, causing them to proliferate and to differentiate into mature effector cells. In fact, eosinophils induced in vitro by IL-5 are fully functional and have been demonstrated to kill antibody-coated schistosomula of *Schistosoma mansoni* and antibody-coated tumor cells.

Since IL-5 plays a major role in the regulation of eosinophils that are prominently involved in allergic inflammation, IL-5 inhibition may have potential therapeutic benefits for various allergies. See Cuss, "Inhibition of Interleukin-5 with a Monoclonal Antibody Attenuates Allergic Inflammation," *Allergy*, 52: 787–794 (1997), incorporated herein by reference.

IL-5 may also act in concert with other hemtopoietic cytokines such as IL-3 and GM-CSF. The three are known for increasing oxidative metabolism, membrane receptor expression and the release of granule proteins as well as for their role in inducing eosinophilopoiesis. In vitro data shows that IL-5 acts in synergy with other activation signals, as in the case of IL-5 and immune complexes. See Desremeux, P. and Capron, M., "Eosinophils in Allergic Reactions", *Current Opin. in Immunol.*, 8: 790–795 (1996), incorporated herein by reference.

The other known activities of IL-5 all relate to regulation of B-cell immune responses. IL-5 was first described as a T-cell activity that induced antigen-stimulated murine B cells to differentiate into both IgM- and IgG-secreting plasma cells. See Takatsu, K., and Tominaga, A., supra. Subsequent studies have shown that IL-5 is the major factor inducing differentiation to immunoglobulin (Ig) production in B cells which were activated by contact with activated T helper cells. Murine IL-5 also augments proliferation of and induces secretion of Ig in a number of B-cell lines. Further, it has similar activity on "in vivo-activated" normal B cells. Murine IL-5 can also enhance the production of IgA in LPS-stimulated B-cell cultures; however, its principal activity is not as a switch-inducing factor, and it does not specifically enhance IgA in T-cell stimulated cultures. Murine IL-5 induces expression of the P55 chain of the IL-2 receptor on normal B cells and, in combination with IL-4, renders these cells responsive to IL-2 stimulation.

Presently, however, the role of IL-5 in human B-cell growth and differentiation remains controversial. IL-5 is inactive in most of the culture systems commonly used to assay human B-cell growth factors and differentiation factors. However, in other assay systems, IL-5 has been shown to be active on human B cells activated with mitogens or activated T-cell clones. Thus, the contribution of IL-5 to the helper activity of T cells in humans is presently not understood.

In vitro biological activities similar to those described above in humans can be postulated for IL-5 in dogs.

In Vivo Activities

In humans, IL-5 appears to be the most specific cytokine for activation of eosinophils. IL-5, IL-3, and GM-CSF may also act in concert to activate eosinophils and basophils, as these three cytokines cross-react on receptors because each cytokine shares a common chain. These cytokines have been identified in late phase reactions in humans. See Desremaux, P., and Capron, M, "Eosinophils in Allergic Reactions", *Current Opin. in Immunol.*, 8: 790–795 (1996).

IL-5 is involved in the eosinophilia that develops during parasitic infections and allergic reactions, but not in the IgG1 or IgE antibody responses associated with these infections. Administration of anti-IL-5 monoclonal antibody blocks the development of both blood and tissue eosinophil responses, but fails to affect IgG1 or IgE secretion. See Cuss, D., "Inhibition of Interleukin-5 with a Monoclonal Antibody Attenuates Allergic Inflammation", *Allergy*, 52: 787–794 (1997).

In vitro experiments suggested that IL-5 is an eosinophil regulator, and numerous in vivo experiments indicate that IL-5 is, in fact, a predominant regulator of eosinophilia. This was readily seen in a series of experiments where the administration of anti-IL-5 antibodies to mice infected with *Nippostrongylus brasiliensis, Schistosoma mansoni, Heligmosomoides polygyrus*, or *Strongyloides venezuelensis* totally blocked the development of eosinophilia. Consistent with these data, mice that have over expressed IL-5 due to the introduction of IL-5 transgenes or IL-5 retroviral constructs are characterized by dramatic increases in eosin counts. In contrast to IL-5 expressing mice, mice that have been genetically engineered to over express either IL-3 or GM-CSF live only a few weeks due to massive tissue infiltration and destruction by the greatly increased numbers of myeloid cells.

In vivo biological activities similar to those described above in humans can be postulated for IL-5 in dogs.

SUMMARY OF THE INVENTION

The present invention relates in part to recombinant DNA molecules, and conservative variants thereof, that encode canine IL-5. Disclosed is an isolated polynucleotide comprising the nucleotide sequence of canine IL-5 of FIG. 1 (SEQ ID NO:1) or its complement.

Also disclosed is an isolated canine IL-5 nucleic acid sequence comprising around 80%, preferably around 85%, preferably around 90%, more preferably around 95%, even more preferably around 97% and most preferably around 99% homology to a nucleic acid sequence of canine IL-5 of FIG. 1 (SEQ ID NO:1) or its complement.

Further disclosed is an isolate canine IL-5 nucleic acid comprising the nucleotide sequence encoding the polypeptide comprising the amino acid sequence of FIG. 1.

Also disclosed is an isolated canine IL-5 polynucleotide comprising around 80%, preferably around 85%, preferably around 90%, more preferably around 95%, even more preferably around 97% and most preferably around 99% homology to a nucleic acid comprising the nucleotide sequence encoding the polypeptide comprising the amino acid sequence of FIG. 1.

Further disclosed is a canine IL-5 polynucleotide comprising at least about 20 consecutive nucleotides, preferably at least about 30 consecutive nucleotides, more preferably at least about 50 consecutive nucleotides, more preferably at least about 100 consecutive nucleotides, more preferably at least about 150 consecutive nucleotides, more preferably at least about 200 consecutive nucleotides, more preferably at least about 250 consecutive nucleotides, more preferably at least about 300 consecutive nucleotides, more preferably at least about 350 consecutive nucleotides, most preferably at least about 400 consecutive nucleotides, of the sequence of FIG. 1, and conservative variants thereof.

These polynucleotides are referred to herein as canine IL-5 polynucleotides.

In another aspect, an isolated canine IL-5 polypeptide comprising the amino acid sequence of FIG. 1 is disclosed.

Also disclosed is an isolated canine IL-5 polypeptide comprising around 80%, preferably around 85%, preferably around 90%, more preferably around 95%, even more preferably around 97%, and most preferably around 99% identity to the canine IL-5 polypeptide of FIG. 1.

Also disclosed is a canine IL-5 polypeptide comprising at least about 7 consecutive amino acids, preferably at least about 10 consecutive amino acids, more preferably at least about 33 consecutive amino acids, more preferably at least about 50 consecutive amino acids, more preferably at least about 66 consecutive amino acids, more preferably at least about 83 consecutive amino acids, more preferably at least about 99 consecutive amino acids, more preferably at least about 116 consecutive amino acids, most preferably at least about 132 consecutive amino acids, of the sequence of FIG. 1 and conservative variants thereof.

In another aspect of the present invention, polypeptides produced using a recombinant expression vector containing a canine IL-5 sequence are set forth.

The above-identified polypeptides are herein referred to as canine IL-5 polypeptides.

In a related aspect, a method is described that uses a polynucleotide encoding canine IL-5 to produce an IL-5 polypeptide. The method comprises expressing the nucleic acid molecule in a transformed host cell and purifying the IL-5 protein, either from the cells or cell debris, or from the medium if the polypeptides are secreted.

In another aspect of the present invention, purified canine IL-5 is provided.

In another aspect of the present invention, recombinant vectors, such as expression vectors, comprising a DNA sequence encoding canine IL-5 are disclosed.

In a further aspect of the present invention, cells comprising the recombinant vectors, which themselves comprise a DNA sequence encoding canine IL-5, are set forth.

In a further related aspect, a method for producing canine IL-5 is disclosed that comprises the steps of inserting a transcription regulatory sequence proximal to the IL-5 gene in a cell comprising that gene, and stimulating production of IL-5 through the regulatory sequence.

In an additional aspect of the present invention, a canine IL-5 polypeptide can be linked to a multiply antigenic peptide so that the multiply antigenic peptide comprises multiple copies of the same peptide or of various peptides. The various peptides can comprise conservative variants of peptides of the invention.

Disclosed is a peptide in accordance with the invention, or a conservative variant thereof, that can be linked to a plant virus particle so that the particle comprises multiple copies of the peptide or of various peptides, in accordance with the invention. The various peptides can comprise conservative variants of peptides of the invention.

Also disclosed are antibodies and other specific binding molecules that bind to canine IL-5 and to mimetopes of IL-5 epitopes.

Disclosed is a method for generating canine autoantibodies directed to the canine IL-5 molecule, said method comprising providing a peptide or a conservative variant thereof, in accordance with the invention, and administering the provided peptide to a dog. The method can further comprise a step of mixing the provided peptide with an adjuvant prior to the administering step, wherein the administering step comprises administering the mixture of the peptide and the adjuvant. The above method may be useful in the treatment and prophylaxis of eosinophil/IL-5 mediated allergic responses in dogs.

DETAILED DESCRIPTION OF THE INVENTION

Definitions

Amino acids: The basic building blocks of proteins, having an amino end and a carboxyl end for the formation of peptide bonds with neighboring amino acids.

TABLE 1

AMINO ACID ABBREVIATIONS

| AMINO ACID | ONE-LETTER SYMBOL | THREE-LETTER SYMBOL |
|---|---|---|
| alanine | A | ala |
| arginine | R | arg |
| asparagine | N | asn |
| aspartic acid | D | asp |
| cysteine | C | cys |
| glutamic acid | E | glu |
| glutamine | Q | gln |
| glycine | G | gly |
| histidine | H | his |
| isoleucine | I | ile |
| leucine | L | leu |
| lysine | K | lys |
| methionine | M | met |
| phenylalanine | F | phe |
| proline | P | pro |
| serine | S | ser |
| threonine | T | thr |
| tryptophan | W | trp |

TABLE 1-continued

AMINO ACID ABBREVIATIONS

| AMINO ACID | ONE-LETTER SYMBOL | THREE-LETTER SYMBOL |
|---|---|---|
| tyrosine | Y | tyr |
| valine | V | val |

Polypeptide: A linear series of amino acids connected one to the other by peptide bonds between the amino and carboxyl groups of adjacent amino acids. As used herein, the term "polypeptide" includes peptides and proteins.

Conservative amino acid substitutions: Substitutions that do not substantially affect the character of the polypeptide. Suitable amino acid variations do not appreciably alter the function of the polypeptide of the invention, although the level of activity may be altered. Activity can be measured in an in vitro test for IL-5 activity, such as an assay for stimulation of eosinophils in culture. The effect of the variations can be reduced by selecting for polypeptide variants that have a minimum of changes in regions of high homology between the canine, mouse and human IL-5 molecules, and are thus conserved regions of the polypeptide. Further, substitutions that replace amino acid(s) with those with similar physical characteristics are preferred. Table 2 lists some preferred amino acid substitutions.

TABLE 2

| Original Residue | Potential Substitutions |
|---|---|
| Ala | val; leu; ile |
| Arg | lys; gln; asn |
| Asn | gln; his; lys; arg |
| Asp | glu |
| Cys | ser |
| Gln | asn |
| Glu | asp |
| Gly | pro; ala |
| His | asn; gln; lys; arg |
| Ile | leu; val; met; ala; phe; norleucine |
| Leu | norleucine; ile; val; met; ala; phe |
| Lys | arg; gln; asn |
| Met | leu; phe; ile |
| Phe | leu; val; ile; ala; tyr |
| Pro | ala |
| Ser | thr |
| Thr | ser |
| Trp | tyr; phe |
| Tyr | trp; phe; thr; ser |
| Val | ile; leu; met; phe; ala; norleucine |

Conservative amino acid additions or deletions: Additions or deletions of amino acids that take place outside of the sequences conserved between canine, human and mouse IL-5 genes and that do not appreciably alter the function of the polypeptide of the invention, although the level of activity may be altered.

Conservative amino acid variants: Amino acid sequences that result from conservative amino acid substitutions.

Nucleotide: A monomeric unit of DNA or RNA nucleic acid sequence consisting of a sugar moiety (pentose), a phosphate, and a nitrogenous heterocyclic base. The four DNA bases are adenine ("A"), guanine ("G"), cytosine ("C") and thymine ("T"). The four RNA bases are A, G, C and uracil ("U"). Nucleotides A and G are purines, whereas C, T, and U are pyrimidines.

Polynucleotide: A linear series of nucleotides connected one to the other by phosphodiester bonds between the 3' and 5' carbons of adjacent pentoses.

Conservative nucleotide substitutions: Nucleotide substitutions that either do not result in changes in the amino acid sequence or that result in conservative amino acid substitutions.

Conservative nucleotide additions or deletions: Additions or deletions of groups of 3 nucleotides (codons) that do not cause a frameshift in translation of a polynucleotide, and that do not create or delete stop codons. These additions or deletions take place outside of the nucleotide sequences conserved between canine, human and mouse IL-5 genes.

Conservative nucleic acid variants: Nucleotide sequences that result from conservative nucleotide substitutions or conservative nucleotide additions or deletions.

Recombinant DNA Molecule: A hybrid DNA sequence comprising at least two nucleotide sequences, the first sequence not normally being found together in nature with the second.

Vector: A plasmid, phage DNA or other DNA sequence, able to replicate in a host cell and capable of carrying an exogenously added DNA sequence for purposes of amplification or expression of the added DNA sequence.

Expression Control Sequence: A DNA sequence of nucleotides that controls and regulates expression of structural genes when operatively linked to those genes.

Regulatory Sequence: A DNA sequence that is necessary for regulation of expression of a coding sequence to which the DNA sequence is operably associated. The nature of regulatory sequences varies depending upon the host organism. For instance, in prokaryotes, regulatory sequences include a promoter, and/or a transcription termination sequence. In eucaryotes, such regulatory sequences include a promoter and/or a transcription termination sequence, and may also include a secretory leader sequence for secretion of a polypeptide attached to the leader.

Mimetope: A variant of the epitope of an antibody, selected by its ability to be bound by antibodies that cross-react with the first antibody.

Pharmaceutically acceptable carrier: Any carrier that is used by persons in the art for administration into a human that does not itself induce any undesirable side effects such as the production of antibodies, fever, etc. This term includes excipients.

Purified or isolated: The molecule so indicated is present in substantial absence of other biological macromolecules of the same species or type.

Specific binding: Binding of one substance to another at a greater binding affinity than background binding. Two substances which exhibit specific binding are referred to as specific binding partners, or as a specific binding pair. An antibody and its antigen are one example of a specific binding pair.

Specific Binding Molecule: A molecule which exhibits specific binding to its corresponding binding partner to form a specific binding pair. As used herein, this definition of specific binding molecule includes but is not limited to monoclonal and polyclonal antibodies, antigen-binding fragments of these antibodies, hybrid antibodies, single-chain antibodies, and recombinant molecules capable of specific binding to a ligand.

Therapeutically effective amount: The amount that is effective for production of a desired result. This amount varies depending upon the health and physical condition of the animal being treated, the capacity of the animal's immune system to synthesize antibodies, the degree of protection desired, the formulation, and other pertinent factors.

DESCRIPTION OF FIGURES

FIG. 1 depicts the nucleic acid sequence, and corresponding amino acids encoded thereby, for canine IL-5 (SEQ ID NOS:1–2).

FIG. 2 shows a comparison between the amino acid sequences of human (SEQ ID NO:7), mouse (SEQ ID NO:8) and dog (SEQ ID NO:2) IL-5.

DETAILED DESCRIPTION OF THE INVENTION

The present invention provides the nucleotide and amino acid sequences of canine IL-5 and conservative variants thereof. It also provides polynucleotides, polypeptides, antibodies and other binding proteins directed to the polypeptides, vectors for replication and expression of the polynucleotides, cells incorporating such vectors, and methods for making the above.

Polynucleotides

In one aspect of the invention, a recombinant DNA molecule, and conservative variants thereof, comprising the DNA sequence of canine IL-5 are disclosed for the first time, as SEQ. ID NO.:1. Also disclosed are the amino acid sequence of canine IL-5, presented as SEQ. ID NO.:2. Described below is the procedure used to obtain these sequences.

In another aspect of the present invention, recombinant vectors, such as expression vectors, comprising a DNA sequence encoding canine IL-5 are set forth. These vectors can include any vectors capable of self-replication within a host cell and into which a canine IL-5 polynucleotide can be cloned. Also included in the invention are expression vectors which have regulatory sequences for the transcription and translation of the inserted polynucleotide into a polypeptide. A wide variety of vectors, including expression vectors, are known and used in the field. For example, pT7Blue® (Invitrogen) was used in the cloning of the canine IL-5 cDNA, as described below.

Cloning and Sequencing of the Canine IL-5 Sequence

Canine interleukin 5 cDNA was cloned from the con-A stimulated canine thymus cell line CF-2TH (ATCC #CRL-1430) by RT-PCR. The cells were cultured in Dulbecco's modified Eagle's medium (GIBCO/BRL) with 0.1 mM non-essential amino acids (JRH Biosciences), 20% fetal bovine serum, at 37° C., 5% $CO_2$. The cells were grown to about 70% confluence, when the medium was changed and 20 µg/ml Con-A for 40 hours. The cells were then harvested by trypsin-EDTA treatment.

Primers for RT-PCR were designed from the conserved sequence resulting from the comparison of known IL-5 sequences (human, bovine and murine). The following sequences are those of the primers used to clone canine IL-5.

SEQ. ID NO.:3 5'primer 5'-CAGTGGTGAAAGAGAC-CTTG-3'

SEQ. ID NO.:4 3'primer 5'-CTCAACTTTCCATTGTC-CACTC-3'

It was predicted that this set of primers would give a PCR product of 271 bp, an oligonucleotide large enough to contain most of the coding region.

PCR was performed as follows. mRNA was prepared from $1 \times 10^6$ Con-A stimulated CF-2TH cells using Invitrogen's Micro-fast Track kit. First strand cDNA was made from the mRNA by the Copy kit. The volume of the cDNA was 20 µl. The PCR reaction was set up using Invitrogen's PCR Optimizer Kit: 1× Buffer B, 1 µl first strand cDNA; 125 ng of each primer; 1 mM dNTP mix; and 0.5 µl of Taq DNA polymerase (5 units/µl) in a final volume of 50 µl.

The PCR conditions were as follows:

Enzyme: Taq polymerase

Buffer: Buffer B, Invitrogen's PCR Optimizer Kit

| 1) | 94° C. | 2 min. | 1 cycle |
|---|---|---|---|
| 2) | 94° C. | 1 min. | 35 cycles |
|   | 55° C. | 2 min. |   |
|   | 72° C. | 3 min. |   |
| 3) | 72° C. | 7 min. | 1 cycle |
| 4) | 4° C. | storage |   |

The PCR reaction generated three specific bands. The most intensive band migrated around 270 bp. This band was cut out and cloned into pT7Blue® vector (Invitrogen). The plasmid DNA was purified and sequenced. The deduced amino acid sequence revealed it included the C-terminus exon end of the canine IL-5 gene.

The N-terminal remainder of canine IL-5 was cloned from genomic DNA using PCR. The right-hand primer was derived from the authentic canine IL-5 C-terminal fragment described above. The left-hand primer was from a region of homology between published human and mouse IL-5 in the region upstream of the IL-5 coding sequence. The primers used were:

SEQ. ID NO:5 left 5'-CTGATTGTTAGAAATTATTCA-TTTCCTC-3'

SEQ. ID NO:6 right 5'-CCATAGCCTATCAGCCAAG-TTC-3'

The cloned fragment was sequenced and was found to encode the missing N-terminal coding sequence.

The complete sequence of the coding region is shown in FIG. 1. FIG. 2 is a comparison of the amino acid sequences of human, mouse and dog IL-5.

In yet another aspect of the present invention, compositions comprising a polynucleotide that has a sequence that is antisense to a DNA sequence encoding a component of canine IL-5 are set forth. The component can be the full canine IL-5 protein. The antisense polynucleotide can be used to modify or block expression of canine IL-5 in vivo. Examples of the state of the art in antisense, including methods for modifying and blocking expression of a gene, can be found in Lichtenstein, ANTISENSE TECHNOLOGY: A PRACTICAL APPROACH, IRL Press (1998), and Schlingensie, ANTISENSE—FROM TECHNOLOGY TO THERAPY: LAB MANUAL AND TEXTBOOK, Blackwell Scientific (1997), both of which are incorporated herein by reference.

Conservative Variants

Also included in the present invention are conservative variants of a canine IL-5 polynucleotide. As defined above, conservative polynucleotide variants have changes in their nucleotide sequence that have minimal or no impact on the function of the encoded polypeptide. Thus, conservative polynucleotide variants include an isolated canine IL-5 nucleic acid sequence comprising around 80%, preferably around 85%, preferably around 90%, more preferably around 95%, even more preferably around 97% and most preferably around 99% homology to a nucleic acid sequence of canine IL-5 of FIG. 1 (SEQ ID NO:1) or its complement.

These conservative variant polynucleotides have substitutions, deletions or additions preferably in regions outside the consensus sequences between human, mouse and canine IL-5 DNA (See FIG. 2), although conservative changes in the nucleotide sequence that do not alter the amino acid sequence can occur anywhere in the polynucleotide sequence. Function of the encoded polypeptide can easily be determined by expressing the polynucleotide in an expression vector, optionally purifying the polypeptide, and performing an in vitro assay of activity. For example, an assay for stimulation of eosinophils in culture can be used to monitor IL-5 activity of the polynucleotide variants.

Also disclosed is an isolated canine IL-5 polynucleotide comprising around 80%, preferably around 85%, preferably around 90%, more preferably around 95%, even more preferably around 97% and most preferably around 99% homology to a nucleic acid comprising the nucleotide sequence encoding the polypeptide comprising the amino acid sequence of FIG. 1.

Partial canine IL-5 polynucleotides are also part of the present invention, e.g., nucleotide sequences comprising at least about 20 consecutive nucleotides, preferably at least about 30 consecutive nucleotides, more preferably at least about 50 consecutive nucleotides, more preferably at least about 100 consecutive nucleotides, more preferably at least about 150 consecutive nucleotides, more preferably at least about 200 consecutive nucleotides, more preferably at least about 250 consecutive nucleotides, more preferably at least about 300 consecutive nucleotides, more preferably at least about 350 consecutive nucleotides, most preferably at least about 400 consecutive nucleotides, of the sequence of FIG. 1, and conservative variants thereof. Such partial polynucleotides can easily be made by several methods, including random sheering of the isolated canine IL-5 polynucleotides, genetically engineering shorter inserts in vectors that are then replicated in host cells followed by isolation of the insert DNA, and synthetic production of the partials.

Polypeptides

In another aspect of the present invention, polypeptides comprising a canine IL-5 sequence are set forth. These polypeptides can be anywhere in size from 7 amino acids to the full length canine IL-5 protein or larger. For example, the present invention includes a canine IL-5 polypeptide comprising at least about 7 consecutive amino acids, preferably at least about 10 consecutive amino acids, more preferably at least about 33 consecutive amino acids, more preferably at least about 50 consecutive amino acids, more preferably at least about 66 consecutive amino acids, more preferably at least about 83 consecutive amino acids, more preferably at least about 99 consecutive amino acids, more preferably at least about 116 consecutive amino acids, most preferably at least about 132 consecutive amino acids, of the sequence of FIG. 1 and conservative variants thereof.

The polypeptides may also be conservative polypeptide variants of canine IL-5, having at least about 80% identity in amino acid sequence to the same sized polypeptide of canine IL-5. Preferably they have at least about 85% identity, more preferably at least about 90% identity, even more preferably at least about 95% identity, more preferably at least about 97% identity; and most preferably at least about 99% identity, and most preferably 100% identity to portions of the canine IL-5 amino acid sequence.

The canine IL-5 polypeptides can be produced using a recombinant expression vector containing the whole or partial DNA sequence for the canine IL-5 gene. Host cells containing the vector are cultured and the polypeptide is separated from the cells by a method well known in the art. For example, if the polypeptide is extracellular, the supernatant can be removed from the cell culture. Otherwise the cells can be lysed and the protein separated from the cell debris. Methods for purifying the polypeptides are well known in the field, such as by size or density gradient, affinity column containing a binding partner to canine IL-5, and SDS-PAGE electrophoresis. These well known techniques are described in Ream, et al., Molecular Biology Techniques: An Intensive Laboratory Course, Academic Press, 1998; Colowick, S. (ed.) Methods in Enzymology: Guide to Molecular Cloning Techniques, Academic Press, 1987, both of which are incorporated by reference in their entirety.

As will be appreciated by those skilled in the art, Canine IL-5 polypeptides also can be generated synthetically.

Antibodies and Other Binding Proteins

Also disclosed are antibodies that bind to canine IL-5, and mimetopes of IL-5 epitopes. A mimetope is a variant of the epitope of an antibody, selected by its ability to be bound by antibodies that cross-react with the first antibody. In one aspect of this invention, mimetopes are prepared in accordance with methodologies known in the art, such as phage display technology. A preferred method for performing phage display technology is accomplished by using a Ph.D. Phage Display Peptide Library Kit. (New England Biolabs, Beverly, Mass.)

Further disclosed is a method for generating canine autoantibodies directed to the canine IL-5 molecule, said method comprising providing a peptide in accordance with the invention or a conservative variant thereof, and administering the provided peptide to a dog. The method can further comprise a step of mixing the provided peptide with an adjuvant prior to the administering step, wherein the administering step comprises administering the mixture of the peptide and the adjuvant. The above method may have potential beneficial therapeutic and prophylactic uses in eosinophil/IL-5 mediated allergic responses in dogs.

A unique approach to generate peptides via T cell dependent responses is contained in EPICOAT™ technology from Axis Genetics of Cambridge, England. Thus, in accordance with an embodiment of the invention, IL-5 epitopes, or conservative variants thereof, are inserted into the coat proteins of a cow pea virus. The virus is thus able to express these peptides on its surfaces, and present them to the immune system in order to induce antibody production. A perceived advantage of this embodiment is that the plant virus proteins are recognized as foreign by the immunized animal. The availability of epitopes on the virus particles bound by T cells induces a T cell dependent antibody response against the inserted self-peptides of interest. Thus, in accordance with the invention, both B and T cell responses to recombinant virus particle containing IL-5 epitopes from a given species are generated. Since cow pea plants are readily grown in abundance in controlled environments, large quantities of Chimeric virus particles (CVPs) containing many copies of peptides in accordance with the invention may be easily generated.

Methods of Use of Canine IL-5

Potential Therapeutic Applications of IL-5

As discussed above, IL-5 is understood to function as the main regulator of eosinophils, a subset of cytotoxic cells capable of killing helminths, parasitic protozoa, and tumor cells in vitro. For example, the presence of eosinophils has been shown to be a positive prognostic indicator in a variety of human tumors. Accordingly, systemic IL-5 administration, or IL-5 gene therapy, may be potentially useful in some canine tumor settings.

On the other hand, eosinophils play an undesirable role in certain allergic and inflammatory reactions, e.g., particularly in the case of asthma in humans. In allergic situations, development of an IL-5 antagonist may potentially allow effective therapeutic intervention.

EXAMPLES

Example 1

Antibodies Against Canine IL-5

In a reading frame beginning with the first nucleotide set forth in FIG. 1 (the reading frame that codes for the native protein), a peptide sequence is encoded. This nucleotide sequence can be translated into a peptide. Peptides are made as in example 1. In accordance with standard methodologies in the art, monoclonal antibodies are prepared to a peptide of at least six contiguous amino acids of the translated sequence. Those antibodies that bind to and inactivate canine IL-5 are selected.

In an alternative, monoclonal antibodies are prepared by phage display technology. A preferred method for performing phage display technology is accomplished by use of a Ph.D. Phage Display Peptide Library Kit. (New England Biolabs, Beverly, Mass.)

Furthermore, mouse monoclonal antibodies may be "caninized" in accordance with methodologies known in the art. See e.g., Reichman, L. et al., "Reshaping human antibodies for therapy", Nature 332: 323–327 (1988). Alternatively, mouse monoclonal antibodies are chimerized with canine antibodies or sequences thereof so as to achieve antibodies which are seen to the recipient host as less immunogenic than standard murine monoclonal antibodies. See e.g., U.S. Pat. No. 5,593,861, "Dog-Mouse Heterohybridoma and Gene Fragment Coding for Constant Region of Canine Immunoglobulins", which is incorporated herein by reference.

These binding molecules, and fragments thereof that retain binding specificity, are screened to determine those which bind to IL-5 in a manner which blocks binding of this cytokine to its receptor on eosinophils.

Example 2

Mimetope Peptide

FIG. 1 sets forth the amino acid sequence of canine IL-5. In addition to a recombinant peptide of at least five contiguous amino acids of the peptide set forth in FIG. 1, variant peptides, i.e., mimetopes, are prepared that elicit antibodies which cross-react with the authentic IL-5 protein. Such mimetopes are prepared in accordance with methodologies known in the art, using randerized peptide libraries and display technologies. A preferred method for performing phage display technology is accomplished by use of a Ph.D. Phage Display Peptide Library Kit. (New England Biolabs, Beverly, Mass.) The phage display technology uses a randomized peptide library instead of authentic IL-5 peptide.

Example 3

ELISA

Recombinant peptides derived from the disclosed amino acid sequence set forth in FIG. 1, or mimetope peptides thereof, are used in combination with monoclonal antibodies which recognize such a peptide and also recognize authentic IL-5 protein, to prepare an immunoassay, such as an ELISA, to detect authentic IL-5 in canine serum. The immunoassay is prepared in accordance with methodologies known in the art. Pursuant to use of such an immunoassay, variations in the levels of IL-5 are found to be predictive of the status of inflammatory conditions such as allergy or arthritis.

Example 4

Antibodies to Mimetopes

FIG. 1 sets forth the amino acid sequence of canine Il-5; this sequence is referred to as the native peptide sequence. Variants of the native peptide sequence are prepared. Preferably, these variants are made relative to a sequence of at least five contiguous amino acids of the native peptide sequence.

In accordance with standard methodologies in the art, monoclonal antibodies are prepared to a variant peptide of the translated sequence. Furthermore, mouse monoclonal antibodies raised in accordance with this example may be "caninized," in accordance with methodologies known in the art. (See e.g., Reichman, L. et al., "Reshaping human antibodies for therapy", Nature 332: 323–327 (1988)). Alternatively, mouse monoclonal antibodies are chimerized with canine antibodies or sequences thereof so as to achieve antibodies which are seen to the recipient host as more allogeneic than standard murine monoclonal antibodies. (See e.g., U.S. Pat. No. 5,593,861, "Dog-Mouse Heterohybridoma and Gene Fragment Coding for Constant Region of Canine Immunoglobulins").

Example 5

Recombinant Binding Molecules to IL-5

Antibodies are prepared in accordance with Examples 2 or 5. By use of methodologies known in the art, such as epitope mapping or phage display technology, the amino acid sequence of the binding site of an antibody in accordance with the invention is identified. A preferred method for performing phage display technology is accomplished by use of a Ph.D.™ Phage Display Peptide Library Kit (New England BioLabs, Beverly, Mass.). The identified binding sequence is then utilized to create a recombinant binding molecule that binds to the same antigen as the antibody.

Example 6

Antagonist to IL-5 Receptor

Native IL-5 is believed to contain two domains. One of these domains serves to bind to the IL-5 receptor on cells such as eosinophils. Another domain serves to activate the maturation of eosinophils. Based on the domains described in humans (sequences available on the NIH gene bank database;, the dog domains were derived through sequence comparison.

Accordingly, recombinant IL-5 proteins are prepared which contain the binding domain which is bound by the IL-5 receptor, but which lack the domain which achieves activation and maturation of the eosinophil.

It is hypothesized that if these peptides were administered to a patient, the peptides would bind to, and therefore block, the IL-5 receptors on eosinophil, but the cells to which these peptides would be bound would not be induced to mature and become activated. Thus, the administration of these recombinant IL-5 proteins may block the maturation or activation of the cells. Accordingly, under this hypothesis, administration of these peptides would interfere with the inflammatory response mediated by infiltration of eosinophils and thus these peptides.

Closing

It is to be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to or equivalent to those described herein can be used in the practice or testing of the invention, the preferred methods and materials are now described. All items of information mentioned herein are fully incorporated herein by reference.

---

What is claimed is:

1. A purified polynucleotide comprising SEQ ID NO:1.
2. A purified nucleic acid probe comprising a polynucleotide that is sense or antisense to a polynucleotide of claim 1.
3. A cloning vector comprising the polynucleotide of claim 1.
4. A recombinant prokaryotic or eukaryotic cell comprising the vector of claim 3.
5. A cell culture comprising cells of claim 4.
6. A cell that expresses a recombinant polypeptide comprising an amino acid sequence encoded by the polynucleotide of claim 1.
7. A cell culture comprising cells of claim 6.
8. A purified polynucleotide comprising the DNA sequence of canine IL-5 (SEQ ID NO:1) or its complement.
9. A vector of claim 3 which is an expression vector.
10. A method for producing a canine IL-5 polypeptide, said method comprising a step of expressing a polypeptide encoded by a cloning vector according to claim 3.
11. A purified nucleic acid consisting essentially of SEQ ID NO:1.

* * * * *

SEQUENCE LISTING

<160> NUMBER OF SEQ ID NOS: 8

<210> SEQ ID NO 1
<211> LENGTH: 405
<212> TYPE: DNA
<213> ORGANISM: Canis familiaris

<400> SEQUENCE: 1

```
atgagaatgc ttctgaattt gagtttgcta gctcttgggg ctgcctatgt ttctgccttt    60
gctgtagaaa atcccatgaa tagactggtg gcagagacct tgacactgct ctccactcat   120
cgaacttggc tgataggcga tgggaacctg atgattccta ctcctgaaaa taaaaatcac   180
caactgtgca ttaaagaagt ttttcagggt atagacacat tgaagaacca aactgcccac   240
ggggaggctg tggataaact attccaaaac ttgtctttaa taaaagaaca catagagcgc   300
caaaaaaaaa ggtgtgcagg agaaagatgg agagtgacaa agttcctaga ctacctgcaa   360
gtatttcttg gtgtaataaa caccgagtgg acaatggaaa gttga              405
```

<210> SEQ ID NO 2
<211> LENGTH: 134
<212> TYPE: PRT
<213> ORGANISM: Canis familiaris

<400> SEQUENCE: 2

```
Met Arg Met Leu Leu Asn Leu Ser Leu Leu Ala Leu Gly Ala Ala Tyr
 1               5                  10                  15

Val Ser Ala Phe Ala Val Glu Asn Pro Met Asn Arg Leu Val Ala Glu
             20                  25                  30

Thr Leu Thr Leu Leu Ser Thr His Arg Thr Trp Leu Ile Gly Asp Gly
         35                  40                  45

Asn Leu Met Ile Pro Thr Pro Glu Asn Lys Asn His Gln Leu Cys Ile
     50                  55                  60

Lys Glu Val Phe Gln Gly Ile Asp Thr Leu Lys Asn Gln Thr Ala His
 65                  70                  75                  80

Gly Glu Ala Val Asp Lys Leu Phe Gln Asn Leu Ser Leu Ile Lys Glu
                 85                  90                  95

His Ile Glu Arg Gln Lys Lys Arg Cys Ala Gly Glu Arg Trp Arg Val
            100                 105                 110

Thr Lys Phe Leu Asp Tyr Leu Gln Val Phe Leu Gly Val Ile Asn Thr
        115                 120                 125

Glu Trp Thr Met Glu Ser
    130
```

<210> SEQ ID NO 3
<211> LENGTH: 20
<212> TYPE: DNA
<213> ORGANISM: Canis familiaris
<220> FEATURE:
<223> OTHER INFORMATION: PCR primer -continued

```
<400> SEQUENCE: 3
cagtggtgaa agagaccttg                                                    20

<210> SEQ ID NO 4
<211> LENGTH: 22
<212> TYPE: DNA
<213> ORGANISM: Canis familiaris
<220> FEATURE:
<223> OTHER INFORMATION: PCR primer

<400> SEQUENCE: 4
ctcaactttc cattgtccac tc                                                 22

<210> SEQ ID NO 5
<211> LENGTH: 28
<212> TYPE: DNA
<213> ORGANISM: Canis familiaris
<220> FEATURE:
<223> OTHER INFORMATION: PCR primer

<400> SEQUENCE: 5
ctgattgtta gaaattattc atttcctc                                           28

<210> SEQ ID NO 6
<211> LENGTH: 22
<212> TYPE: DNA
<213> ORGANISM: Canis familiaris
<220> FEATURE:
<223> OTHER INFORMATION: PCR primer

<400> SEQUENCE: 6
ccatagccta tcagccaagt tc                                                 22

<210> SEQ ID NO 7
<211> LENGTH: 134
<212> TYPE: PRT
<213> ORGANISM: Homo sapiens
<220> FEATURE:
<223> OTHER INFORMATION: Interleukin 5

<400> SEQUENCE: 7

Met Arg Met Leu Leu His Leu Ser Leu Leu Ala Leu Gly Ala Ala Tyr
 1               5                  10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130
```

```
<210> SEQ ID NO 8
<211> LENGTH: 133
<212> TYPE: PRT
<213> ORGANISM: Mus musculus
<220> FEATURE:
<223> OTHER INFORMATION: Interleukin 5

<400> SEQUENCE: 8

Met Arg Arg Met Leu Leu His Leu Ser Val Leu Thr Leu Ser Cys Val
 1               5                  10                  15

Trp Ala Thr Ala Met Glu Ile Pro Met Ser Thr Val Val Lys Glu Thr
                20                  25                  30

Leu Thr Gln Leu Ser Ala His Arg Ala Leu Leu Thr Ser Asn Glu Thr
            35                  40                  45

Met Arg Leu Pro Val Pro Thr His Lys Asn His Gln Leu Cys Ile Gly
    50                  55                  60

Glu Ile Phe Gln Gly Leu Asp Ile Leu Lys Asn Gln Thr Val Arg Gly
65                  70                  75                  80

Gly Thr Val Glu Met Leu Phe Gln Asn Leu Ser Leu Ile Lys Lys Tyr
                85                  90                  95

Ile Asp Arg Gln Lys Glu Lys Cys Gly Glu Glu Arg Arg Arg Thr Arg
                100                 105                 110

Gln Phe Leu Asp Tyr Leu Gln Glu Phe Leu Gly Val Met Ser Thr Glu
            115                 120                 125

Trp Ala Met Glu Gly
        130
```